United States Patent
Linberg

(12) 
(10) Patent No.: US 6,385,593 B2
(45) Date of Patent: May 7, 2002

(54) APPARATUS AND METHOD FOR AUTOMATED INVOICING OF MEDICAL DEVICE SYSTEMS

(75) Inventor: Kurt R. Linberg, Eden Prairie, MN (US)

(73) Assignee: Medtronic, Inc., Minneapolis, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/430,208

(22) Filed: Oct. 29, 1999

(51) Int. Cl.[7] .............................................. G60F 17/60
(52) U.S. Cl. ....................................................... 705/28
(58) Field of Search ........................................... 705/24

(56) References Cited

U.S. PATENT DOCUMENTS

| | | | |
|---|---|---|---|
| 4,494,950 A | | 1/1985 | Fishell ........................ 604/66 |
| 4,830,757 A | * | 5/1989 | Lynch et al. ................. 210/742 |
| 4,886,064 A | | 12/1989 | Strandberg .................. 128/419 |
| 4,987,897 A | | 1/1991 | Funke .......................... 128/419 |
| 5,142,566 A | * | 8/1992 | Meschi ......................... 379/98 |
| 5,321,618 A | | 6/1994 | Gessman ............... 364/413.06 |
| 5,377,114 A | * | 12/1994 | Gross .......................... 364/465 |
| 5,752,976 A | | 5/1998 | Duffin et al. ................. 607/32 |
| H1743 H | * | 8/1998 | Graves et al. ......... 364/479.06 |

FOREIGN PATENT DOCUMENTS

| | | |
|---|---|---|
| JP | 6-296633 | * 10/1994 |
| WO | WO 99/14882 | 3/1999 |

OTHER PUBLICATIONS

"Retrofitting software safety in an implantable medical device" by R. Mojdehrakhsh, Wei–Tek Tsai, S. Kirani and L. Elliott, IEEE Software, Jan. 1994, vol. 11, No. 1, pp. 41–50.*

"Implantable medical device with multi–layered ceramic enclosure" by B. A. Hassler, J. Donders and H. Kolnaar, Proceedins 1996 International Symposium on Microelectronics, SPIE vol. 2920, pp. 488–492, Oct. 8–10, 1996.*

* cited by examiner

Primary Examiner—Kenneth R. Rice
(74) Attorney, Agent, or Firm—Girma Wolde-Michael

(57) ABSTRACT

A system and method for remote invoicing and inventory control of medical components of an implantable medical device system upon implantation into a patient is described. The system includes at least one medical component implanted in a patient. A programmer is capable of identifying each medical component implanted in the patient. A remote expert data center globally accessible to the programmer is connected to the programmer via an interface. An invoice module positioned on the remote expert data center receives information identifying each medical component implanted in the patient and prepares an invoice including each medical component implanted into the patient. An inventory module updates records regarding inventory of each implanted medical component.

5 Claims, 8 Drawing Sheets

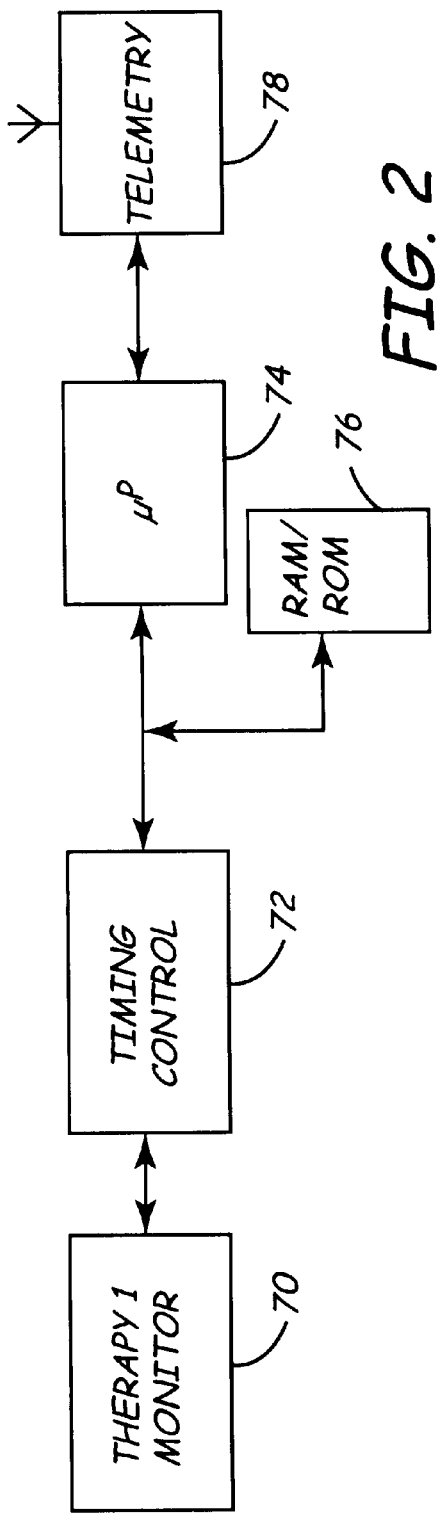
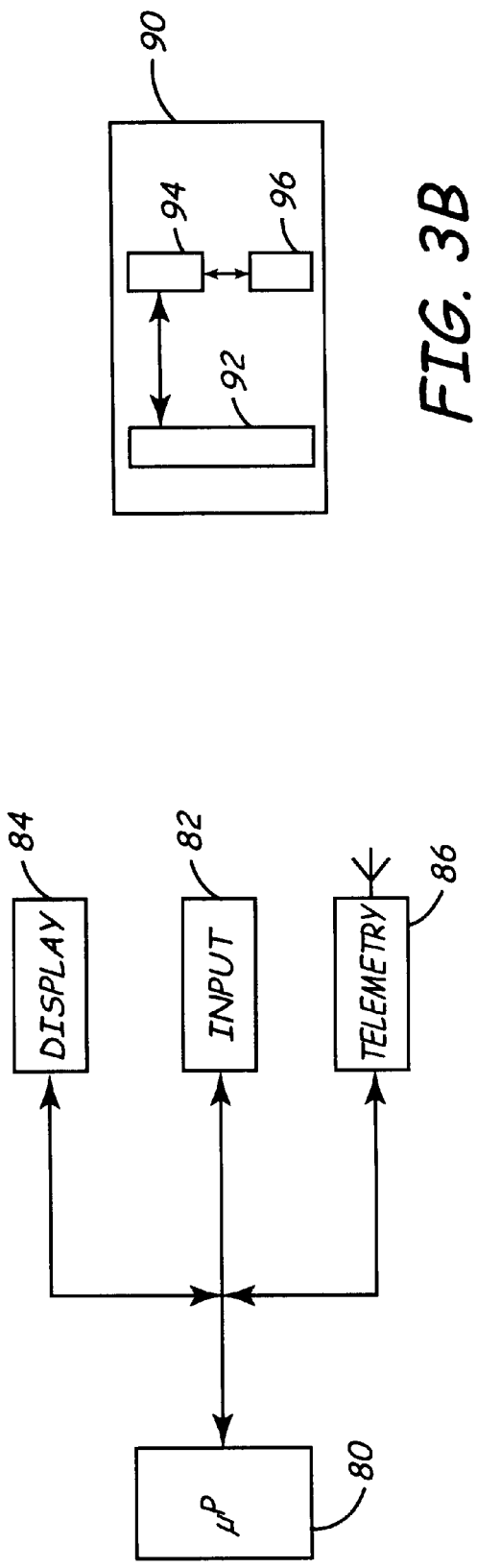
FIG. 2
FIG. 3B
FIG. 3A

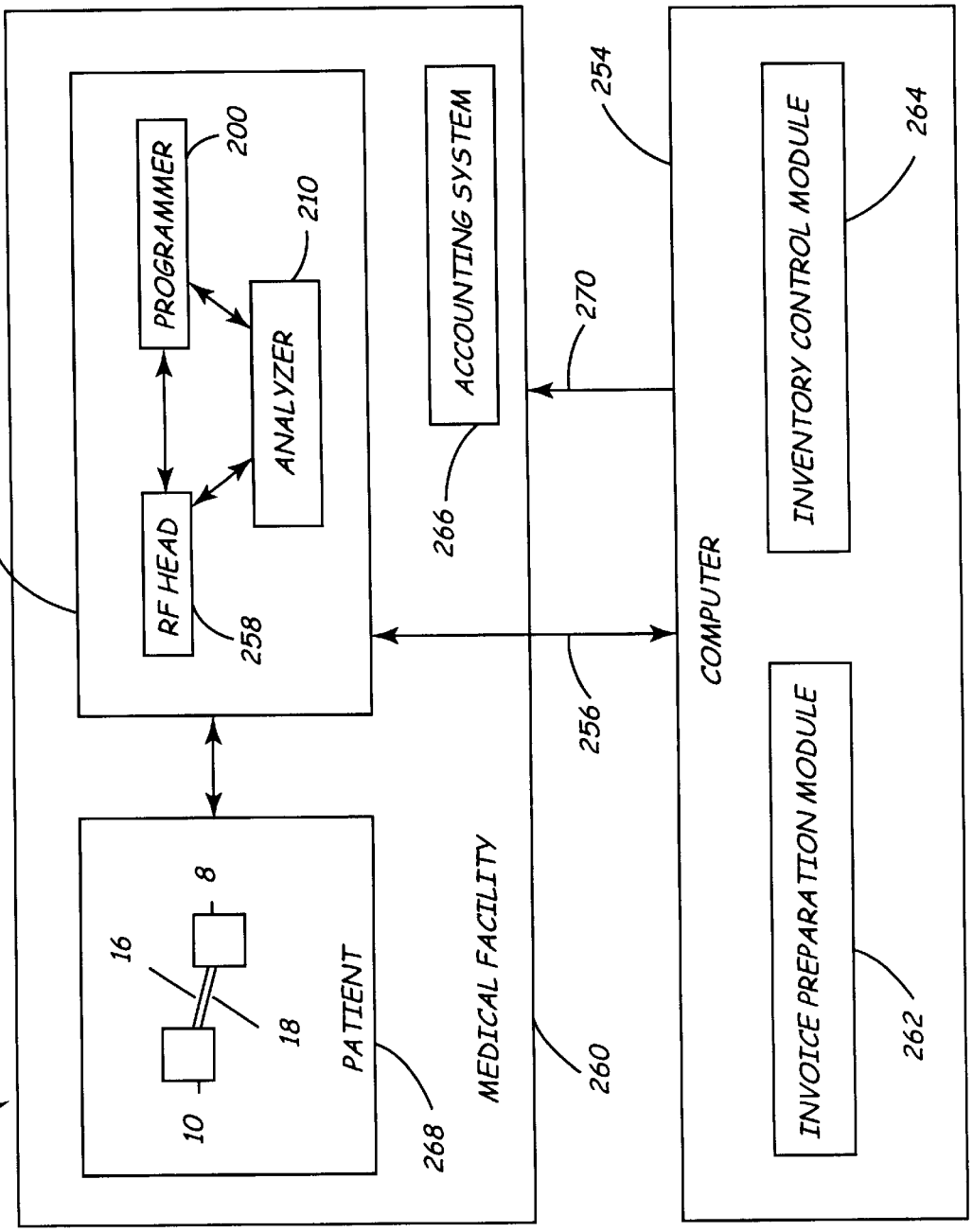

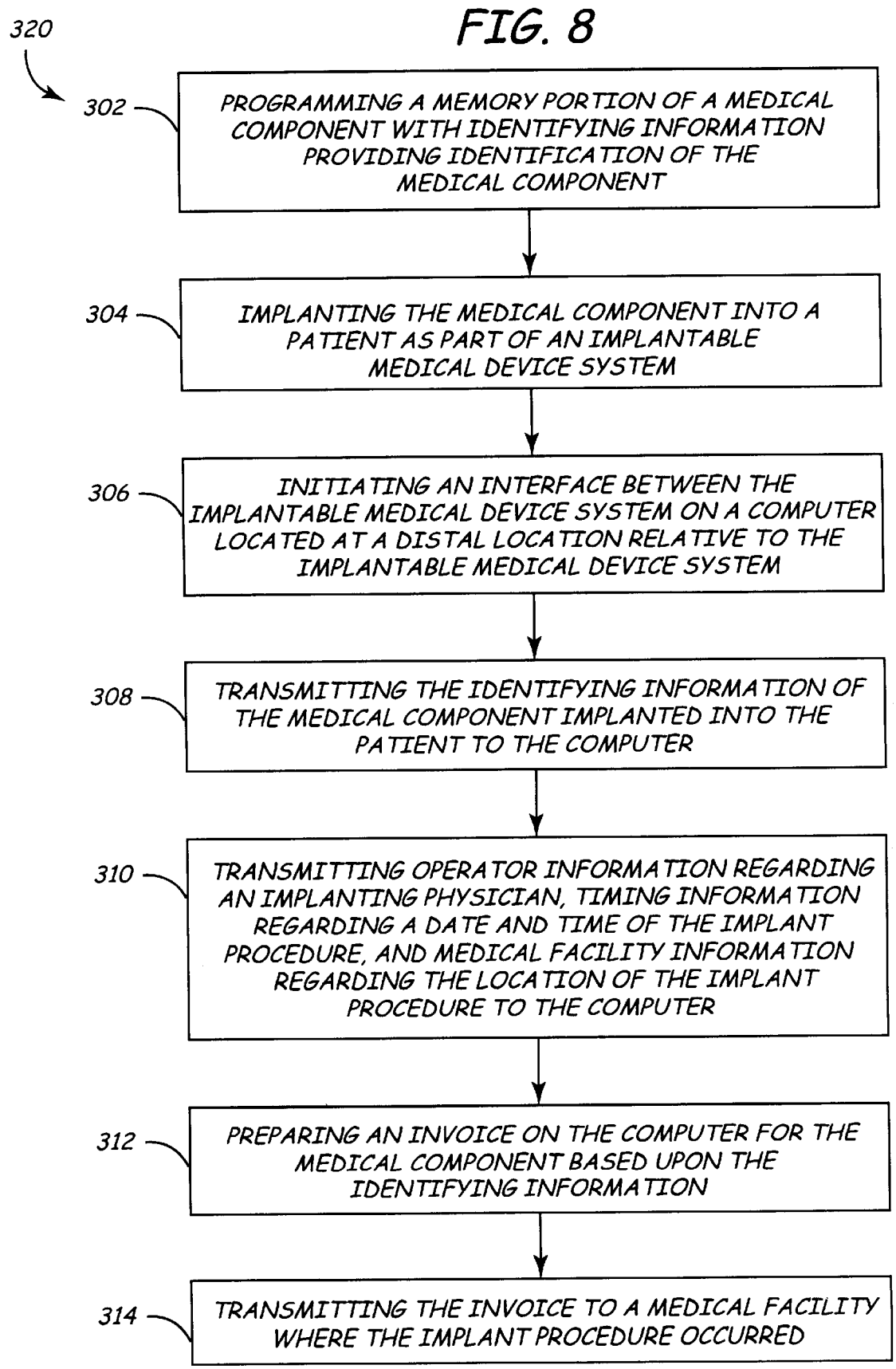

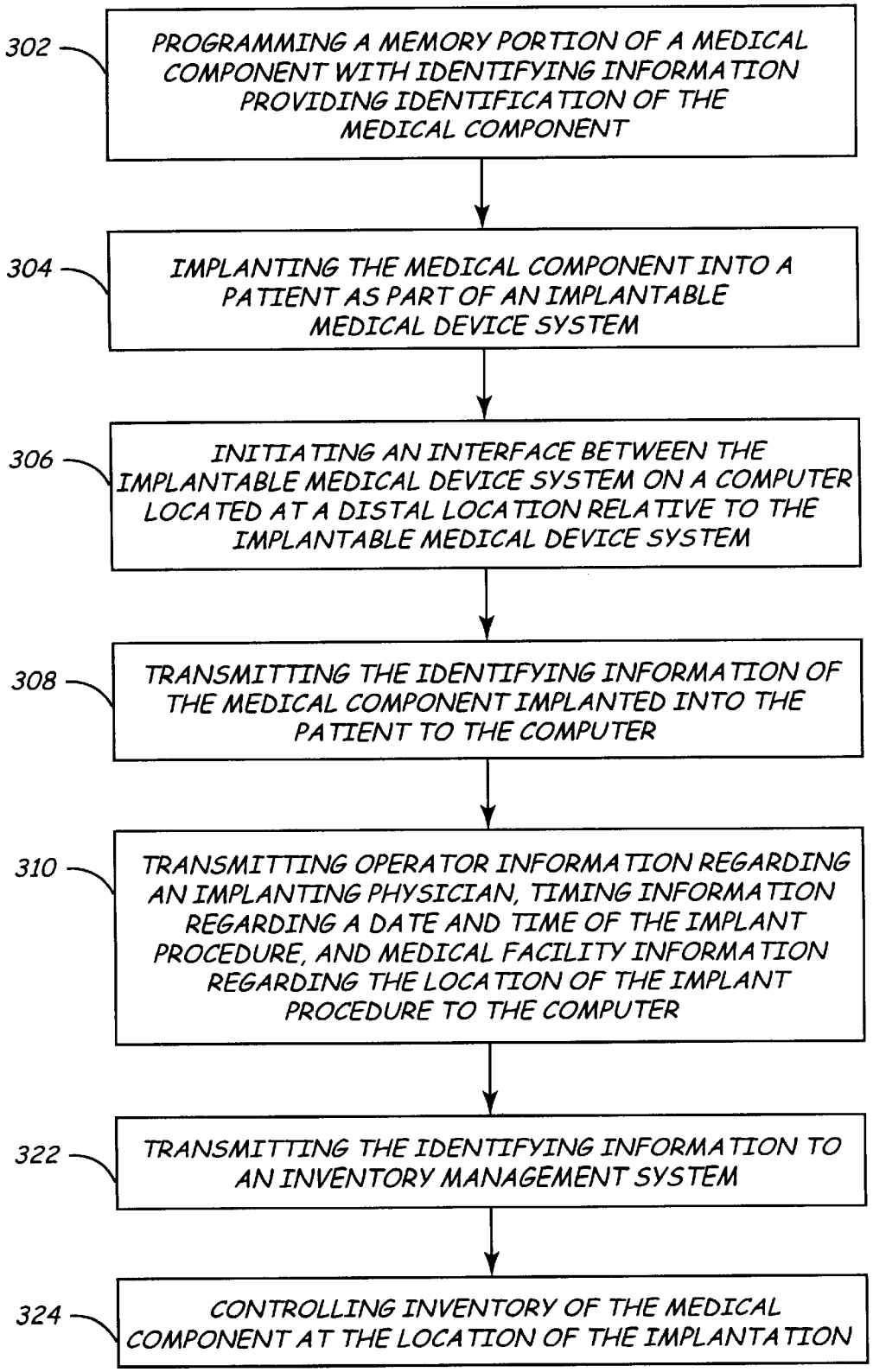

APPARATUS AND METHOD FOR AUTOMATED INVOICING OF MEDICAL DEVICE SYSTEMS

THE FIELD OF THE INVENTION

The present invention relates generally to medical device systems. Specifically, the invention pertains to a remote bi-directional communications with one or more programming devices, that are associated with implantable medical devices. Generally, the invention relates to an integrated system and method of bi-directional telecommunications between a web-based expert data center and at least one programmer, utilizing various types of network platforms and architecture to implement, in the programmer, distance-based troubleshooting, maintenance, upgrade, information and administrative services thereby providing an economical and highly interactive system for therapy and clinical care. More specifically, the present invention provides an automatic invoice of medical components used in conjunction with an implantable medical device systems.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide medical services in a time and place independent manner.

Prior art methods of clinical services are generally limited to in-hospital operations. For example, if a physician needs to review the performance parameters of an implantable medical device (IMD) in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinical center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose a serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and present procedures relating to an IMD. Generally, a report should be generated each time an external medical component such as a programmer and/or analyzer is connected to the IMD. Various information should be contained in the report including an identification of all such external components used during a procedure. Specifically, all peripheral and major devices that are used in down linking to the IMD need to be reported. Presently, there is no automated system for providing an automated report of all the major components used in a procedure involving communications with an IMD. The current practice is for a medical person to physically record or enter data related to the devices used in the down linking procedure. One of the limitations of this procedure is the fact that it is error prone and often requires rechecking of the data to verify accuracy. Further, the current method does not lend itself to a centralized network where identification and related data, for globally distributed programmers and peripheral devices used in conjunction with IMDS, could be stored.

A further limitation of the prior art relates to the management of multiple implantable devices in a single patient. Advances in modern patient therapy and treatment have made it possible to implant a number of devices in a patient. For example, implantable devices such as a defibrillator or a pacer, a neural implant, a drug pump, a separate physiologic monitor and various other implantable devices may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the performance of the implantable devices on a regular, if not a continuous, basis to ensure optimal patient care. In the absence of other alternatives, this imposes a great burden on the patient if a hospital or clinic is the only center where the necessary frequent follow up, evaluation and adjustment of the medical devices could be made. Moreover, even if feasible the situation would require the establishment of multiple service areas or clinic centers to provide adequate service to the burgeoning number of multi-implant patients worldwide. Accordingly, it is vital to have a programmer unit that would connect to a remote expert medical center to provide access to expert systems and import the expertise to a local environment. This approach would enable unencumbered access to the IMD or the patient. Further, the proliferation of patients with multi-implant medical devices worldwide has made it imperative to provide remote services. Thus, frequent use of programmers to communicate with the IMD and provide various remote services, consistent with the disclosure contained in U.S. patent application Ser. No. 09/426,741 entitled "Apparatus and Method for Remote Troubleshooting, Maintenance and Upgrade of Implantable Device Systems," filed on Oct. 26, 1999, U.S. patent application Ser. No. 09/429,956, entitled "Apparatus and Method for Remote Self-Identification of Components in Medical Device Systems", filed Oct. 29, 1999, and U.S. patent application Ser. No. 09/429,960, entitled "Apparatus and Method to Automatic Remote Software Updates of Medical Device Systems" filed Oct. 29, 1999, incorporated by reference herein in their entireties, has become an important aspect of patient care.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, or the programmer, and a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD.

Yet another example of sensing and communications system with a plurality of interactive implantable devices is disclosed by Stranberg in U.S. Pat. No. 4,886,064, issued Dec. 12, 1989. In this disclosure, body activity sensors, such as temperature, motion, respiration and/or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications to enable remote troubleshooting, maintenance and upgrade from outside the patient's body because the processor/programmer is internally located in the patient forming an integral part of the heart pacer.

Yet another prior art reference provides a multi-module medication delivery system as disclosed by Fischell in U.S Pat. No. 4,494,950 issued Jan. 22, 1985. The disclosure relates to a system consisting a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose an external programmer for telemetrically programming the modules.

Yet another example of remote monitoring of implanted cardioverter defibrillators is disclosed by Gessman in U.S. Pat. No. 5,321,618 issued. In this disclosure a remote apparatus is adapted to receive commands from and transmit data to a central monitoring facility over telephone communication channels. The remote apparatus includes equipment for acquiring a patient's ECG waveform and transmitting that waveform to the central facility over the telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

One of the many limitations of the apparatus and method disclosed in the Gessman patent is the fact that the segment, which may be construed to be equivalent to a programmer, is not remotely adjustable from the central monitoring device. The segment merely acts as a switching station between the remote apparatus and the central monitoring station.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the devices at the patient monitoring station may be remotely updated, maintained and tuned to enhance performance or correct errors and defects.

Another example of a telemetry system for implantable medical devices is disclosed in Duffin et al, U.S. Pat. No. 5,752,976, issued May 19, 1998, incorporated by reference herein in its entirety. Generally, the Duffin et al disclosure relates to a system and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Although the Duffin et al disclosure provides significant advances over the prior art, it does not teach a communications scheme in which a programmer is remotely debugged, maintained, upgraded or modified to ultimately enhance the support it provides to the implantable device with which it is associated. Specifically, the Duffin et al disclosure is limited to notifying remote medical support personnel or an operator about impending problems with an IMD and also enables constant monitoring of the patient's position worldwide using the GPS system. However, Duffin et al does not teach the remote programming scheme contemplated by the present invention.

In a related art, Thompson discloses a patient tracking system in a copending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the remote programming concepts advanced by the present invention are not within the purview of the Thompson disclosure because there is no teaching of a web-based environment in which a programmer is remotely evaluated and monitored to effect functional and parametric tune up, upgrade and maintenance as needed. Further in Thompson, the components of the programmer cannot be interrogated for remote identification.

Yet in another related art, Ferek-Petric discloses a system for communication with a medical device in a co-pending application, Ser. No. 09/348,506 which is incorporated by reference herein in its entirety. The disclosure relates to a system that enables remote communications with a medical device, such as a programmer. Particularly, the system enables remote communications to inform device experts about programmer status and problems. The experts will then provide guidance and support to the remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek-Petric's invention advances the art in communications systems relating to interacting with a programmer via a communication medium such as the Internet, the system does neither propose nor suggest remote programming, debugging and maintenance of a programmer without the intervention of a service person. Further, Ferek-Petric's disclosure does not disclose a remote interrogation scheme to identify components used in a programmer-IMD interaction procedure.

Specifically, generating an invoice for implanted medical components implanted in a patient and maintaining and controlling inventory for implantable components are critical issues for the medical device industry. For example, at any one time, millions of dollars of medical components associated with an implantable medical system have been implanted into the patient population. However, there is often a time delay between the implant procedure and both the billing for the implanted components and the inventoring of the implanted components.

Presently, once an implant procedure of a medical device is completed, various procedures must occur regarding inventory control and billing for the implanted components. First, a member of the hospital or medical facility where the implant procedure took place must notify a representative of the company that sold the medical components to the hospital or medical facility that an implant procedure has occurred. The medical facility member will indicate that specific medical components, such as pacing and/or sensing leads and a pacemaker pulse generator, have been implanted into a patient. The notification is normally done by preparing paperwork regarding the implanted components and forwarding the paperwork to the representative. The representative must fill out additional paper work regarding the medical components which were implanted and forward the paperwork to a central location. An invoice is prepared at the central location itemizing the implanted medical components, and the hospital or medical facility where the implant procedure occurred is billed accordingly. The information regarding the implant procedure is also forwarded to an inventory department of the company so that the quantity of medical components at a specific hospital or medical facility can be monitored and controlled. This entire process may take weeks or even months to be completed.

The above-discussed procedure for preparing an invoice and for controlling inventory is both time consuming and expensive. Therefore, there is a need for a procedure which will properly control inventory and invoicing of external and implanted medical components associated with an implant procedure.

Accordingly it would be advantageous to provide a system in which a programmer could uplink to a remote expert data center to import enabling software for self-diagnosis, maintenance and upgrade of the programmer. Yet another desirable advantage would be to provide a system to implement the use of remote expert systems to manage a programmer on a real-time basis. A further desirable advantage would be to provide a communications scheme that is compatible with various communications media, to promote a fast uplink of a programmer to remote expert systems and specialized data resources. Yet another desirable advantage would be to provide a high speed communications scheme to enable the transmission of high fidelity sound, video and data to advance and implement efficient remote data management of a clinical/therapy system via a programmer thereby enhancing patient clinical care. As discussed herein below, the present invention provides these and other desirable advantages.

SUMMARY OF THE INVENTION

The present invention overcomes the disadvantages and limitations of the prior art by providing a method and apparatus for remote invoicing of a medical component used in conjunction with an implantable medical device system in a patient.

The present invention generally relates to a communications scheme in which a remote web-based expert data center interacts with a patient having one or more implantable medical devices (IMDs) via an associated external medical device, preferably a programmer, located in close proximity to the IMDs. Some of the most significant advantages of the invention include the use of various communications media between the remote web-based expert data center and the programmer to remotely exchange clinically significant information including identification of specific components of the programmer.

In the context of the present invention, one of the many aspects of the invention includes a real-time access of a programmer to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to the IMDs, as needed.

In yet another context of the invention, the critical components and embedded systems of the programmer are remotely identified, maintained, debugged and/or evaluated to ensure proper functionality and performance by down linking expert systems and compatible software from the web-based expert data center.

In a further context of the invention, a programmer is remotely identified monitored, assessed and upgraded as needed by importing expert systems from a remote expert data center via a wireless or equivalent communications system. The operational and functional software of the embedded systems in the programmer may be remotely adjusted, upgraded or changed as apparent. Some of the software changes may ultimately be implemented in the IMDs as needed by down linking from the programmer to the IMDs. Further, specific components used in programmer-IMD interface will be identified and documented to comply with medical standards.

Yet another context of the invention includes a communications scheme that provides a highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communication systems. However, it should be noted that the communication systems, in the context of this invention, are interchangeable and may relate to various schemes of cable, fiber optics, microwave, radio, laser and similar communications or any practical combinations thereof.

Some of the distinguishing features of the present invention include the use of a robust web-based expert data center to manage the programmer-IMD events and identify the programmer components used therein and tune the operational and functional parameters of a programmer in real-time. Specifically, the invention enables remote diagnosis, maintenance, upgrade, performance tracking, tuning and adjustment of a programmer from a remote location. Although the present invention focuses on the remote real-time monitoring and management of the programmer, some of the changes and upgrades made to the programmer could advantageously be transferred to the IMDs. This is partly because some of the performance parameters of the programmer are functionally parallel to those in the IMDs. Thus, one additional benefit of the present invention is an enhancement of the programmer may be implemented, on a proactive basis, in the IMDs by down linking from the programmer thereby upgrading the IMDs to promote the patient's well being.

Yet one of the other distinguishing features of the invention includes the use a highly flexible and adaptable communications scheme to promote continuous and real-time communications between a remote expert data center and a programmer associated with a plurality of IMDs. The IMDs are structured to share information intracorporeally and may interact with the programmer, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs as needed.

Further, the present invention provides significant advantages over the prior art by enabling remote automated self-identification information of a programmer. The automated self-identification scheme is compatible with a global preferably web-based data center which is configured to interrogate and obtain the identification of components. Primarily, the component-identification procedure relates to the programmer-IMD sessions. Components used in these sessions are identified and centrally logged for reference and compliance requirements. Generally, the web-based expert data center will interrogate the programmer to identify components used in the sessions.

The invention provides significant compatibility and scalability to other web-based applications such as telemedicine and emerging web-based technologies such as tele-immersion. For example, the system may be adapted to webtop applications in which a webtop unit may be used to uplink the patient to a remote data center for non-critical information exchange between the IMDs and the remote expert data center. In these and other web-based similar applications the data collected, in the manner and substance of the present invention, may be used as a preliminary screening to identify the need for further intervention using the advanced web technologies.

In the context of the system and method of the invention, several advantages are provided including: (a) the ability to provide a remote connection between a programmer and a centralized remote expert data center; (b) the ability to transmit identification information for components of the programmer to the remote expert data center; (c) the ability to transmit information relating to a location of an implant procedure to a remote expert data center; (d) the ability to transmit information relating to a data and a time of an implant procedure to a remote expert data center; (e) the ability to remotely and automatically generate an itemized bill including all implemented medical components during an implant procedure; (f) the ability to automatically forward an itemized bill including all implemented medical components from a remote expert data center to a medical facility where the implant procedure took place; and (g) the ability to automatically and remotely generate an inventory including all medical components of implanted devices in a patient and an ability to automatically forward the inventory to an inventory management system.

The system and method of the invention has certain features, including a data communications link/connection between a programmer used in conjunction with IMDs and a remote expert data center. The programmer is located at a location distinct from the location of the remote expert data center. The invention further includes a medical instrument capable of identifying each medical component implanted into a patient. The invention further includes an information preparation module and data communication with the remote expert data center which receives information identifying each implanted medical component and prepares an invoice listing each of the implanted medical components. The invention further includes an inventory control module and a data communication scheme with the information network that receives the information identifying each implanted medical component and forwards the identification data to an inventory management system.

Other advantages, and features of the invention will become apparent by referring to the appended drawings, detailed description, and claims.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 2 is a block diagram representing the major components of an IMD;

FIG. 3A is a block diagram presenting the major components of a programmer or webtop unit;

FIG. 3B is a block diagram representing a laser transceiver for high speed transmission of voice, video and other data;

FIG. 7 is a detailed block diagram showing an overall programmer invoice and inventory system used in conjunction with the present invention.

FIG. 8 is a flow chart illustrating a method of remote invoicing of a medical component used in conjunction with an implantable medical device system.

FIG. 9 is a flow chart illustrating a method of remotely controlling inventory of a medical component used in conjunction with an implantable medical device system.

DESCRIPTION OF THE PREFERRED EMBODIMENTS

Figure 1:
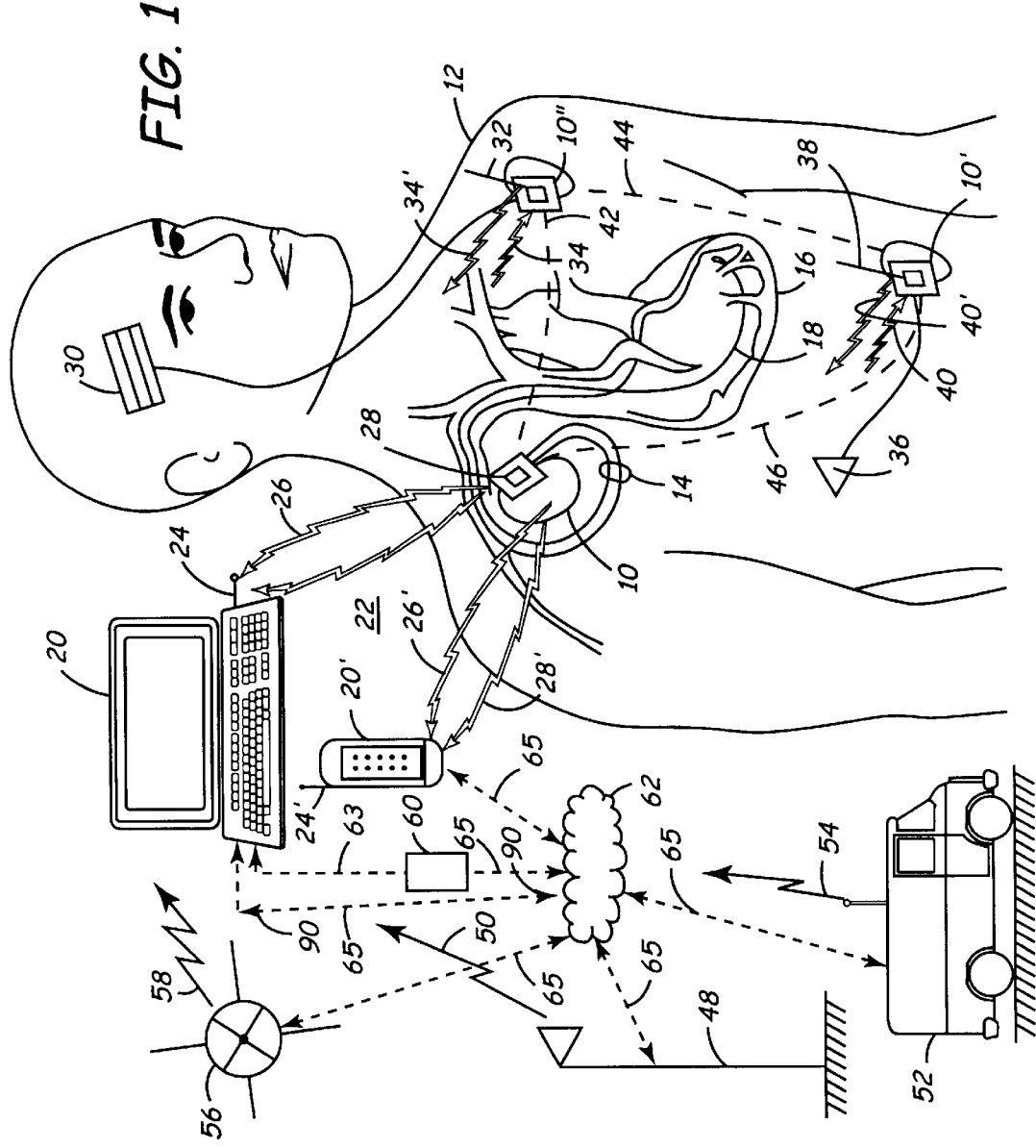
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bidirectional wireless communications system between programmer 20, webtop unit 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and webtop unit 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or webtop unit 20'. Accordingly programmer 20 and webtop unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or webtop unit 20' and data center 62. The communications link between Programmer 20 or webtop unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, webtop unit 20', mobile vehicle 52 and satellite 56 are in communications with data center 62 via wireless link 65. Further, mobile system 52 and satellite 56 are in wireless communications with programmer 20 or webtop unit 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably bluetooth chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

FIG. 2 illustrates typical components of an IMD, such as those contemplated by the present invention. Specifically, major operative structures common to all IMDs 10, 10' and 10" are represented in a generic format. In the interest of brevity, IMD 10 relative to FIG. 2 refers to all the other IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD 10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microremote expert data center 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of micro remote expert data center 74.

Further referring to FIG. 3A, programmer 20 is a personal remote expert data center type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real time data. Display screen 84 may also display plinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or webtop unit 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
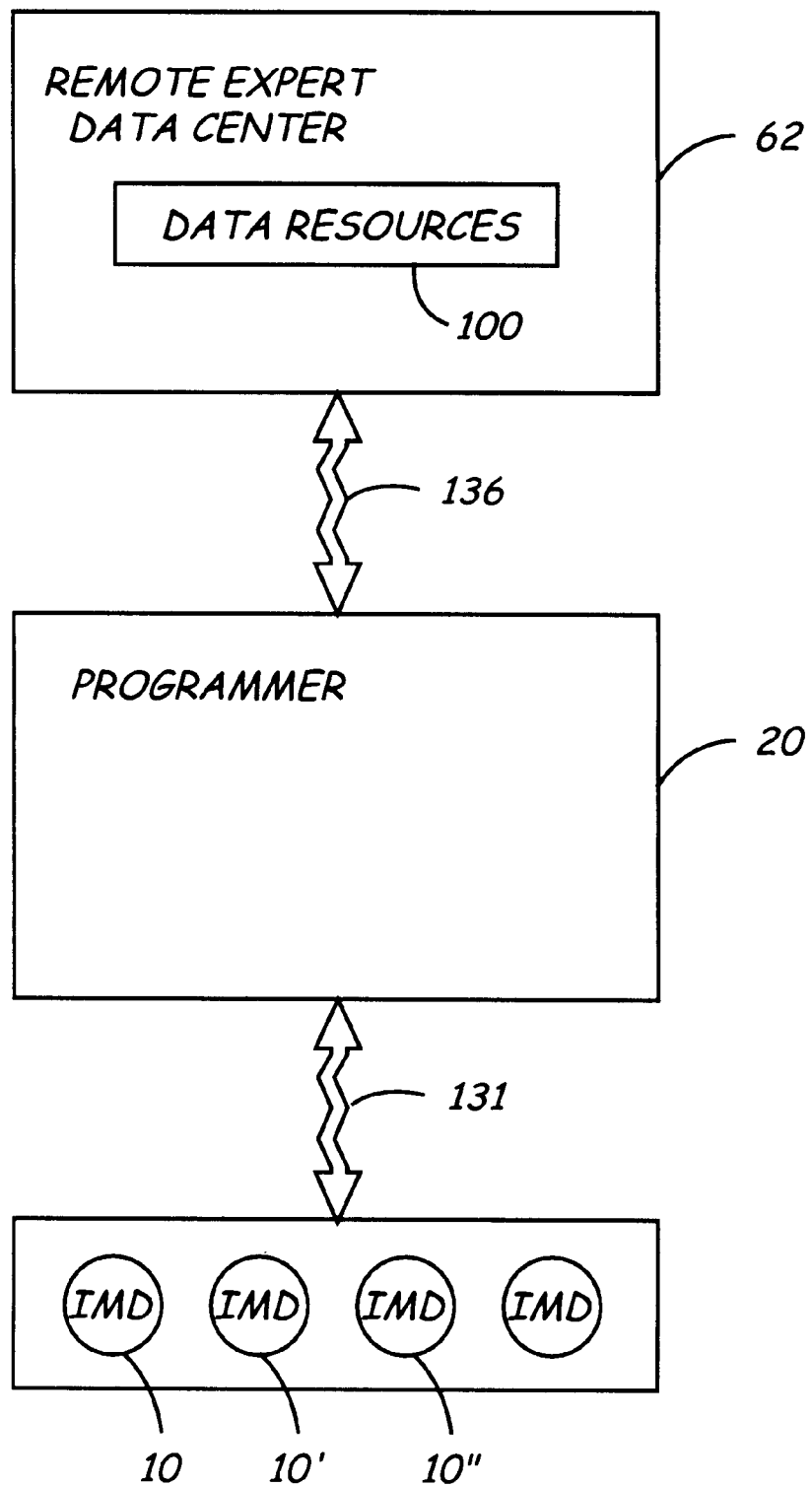
FIG. 4 is a block diagram illustrating the organizational structure of the wireless communication system in accordance with the present invention.

FIG. 4 is a simplified block diagram illustrating the principal systems of the invention. The Remote expert system or data center 62 includes data resource 100. As discussed hereinabove, data center 62 is preferably in wireless communications with programmer 20. The medium of communications between programmer 20 and data center 62 may be selected from one or a combination of several cable and wireless systems discussed hereinabove. Further, programmer 20 is in wireless communications with a number of IMDs, such as shown in FIG. 1. Although three IMDs are shown for illustrative purposes, it should be noted that several IMDs may be implemented and the practice of the present invention does not limit the number of implants per se.

Figure 5:
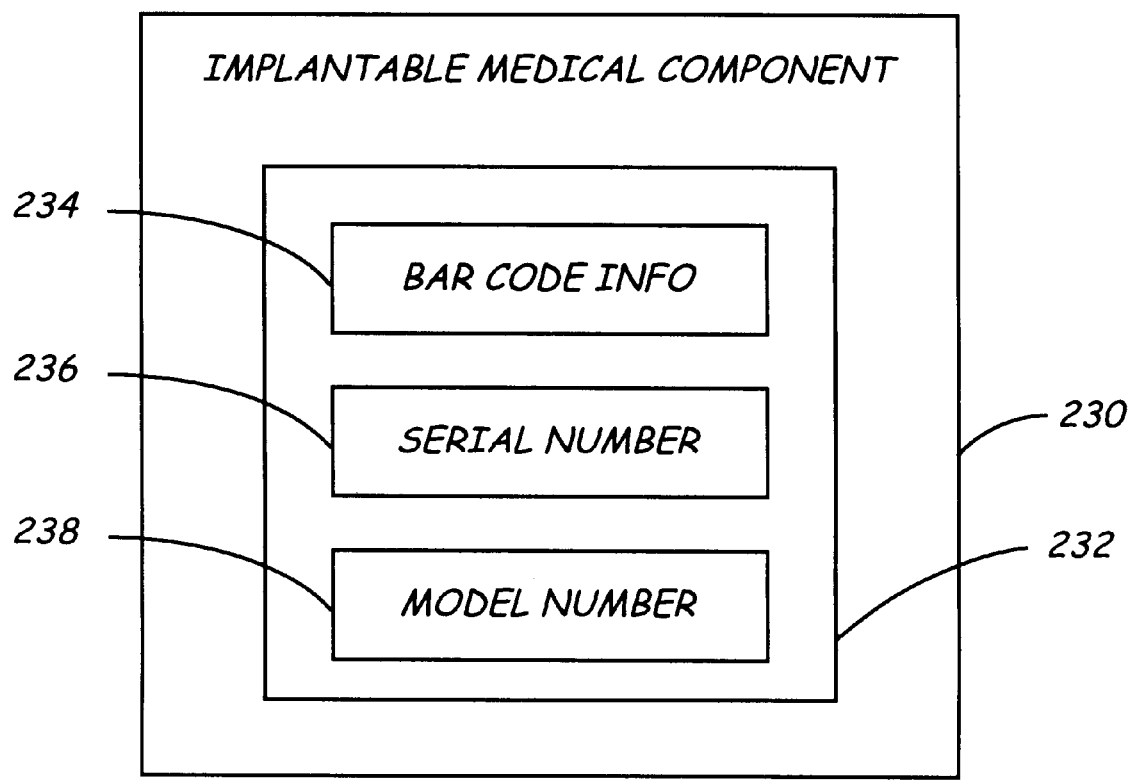
FIG. 5 is a block diagram of an implantable medical component used in conjunction with an implantable medical device.

FIG. 5 is a block diagram illustrating an implantable medical component which is implanted in a patient under medically accepted standard implantation procedures. For example, implantable medical component 230 represents IMD 10, pacing and sensing leads 16 and 18, or any other implantable medical component which is implanted in a patient. Implantable medical component 230 includes memory component 232 which can be a microprocessor, a memory component of a read-only memory (ROM) device, or any other component capable of storing information. Memory component 232 stores identification information which specifically identifies implantable medical component 230. Memory component 232 stores various information which identifies implantable medical component 230. For example, memory component 232 stores bar code information 234, serial number 236, and model number 238; each of which provides specific identifying information about implantable medical component 230. Therefore, by retrieving information from memory component 232, implantable medical component 230 can be specifically identified.

Figure 6:
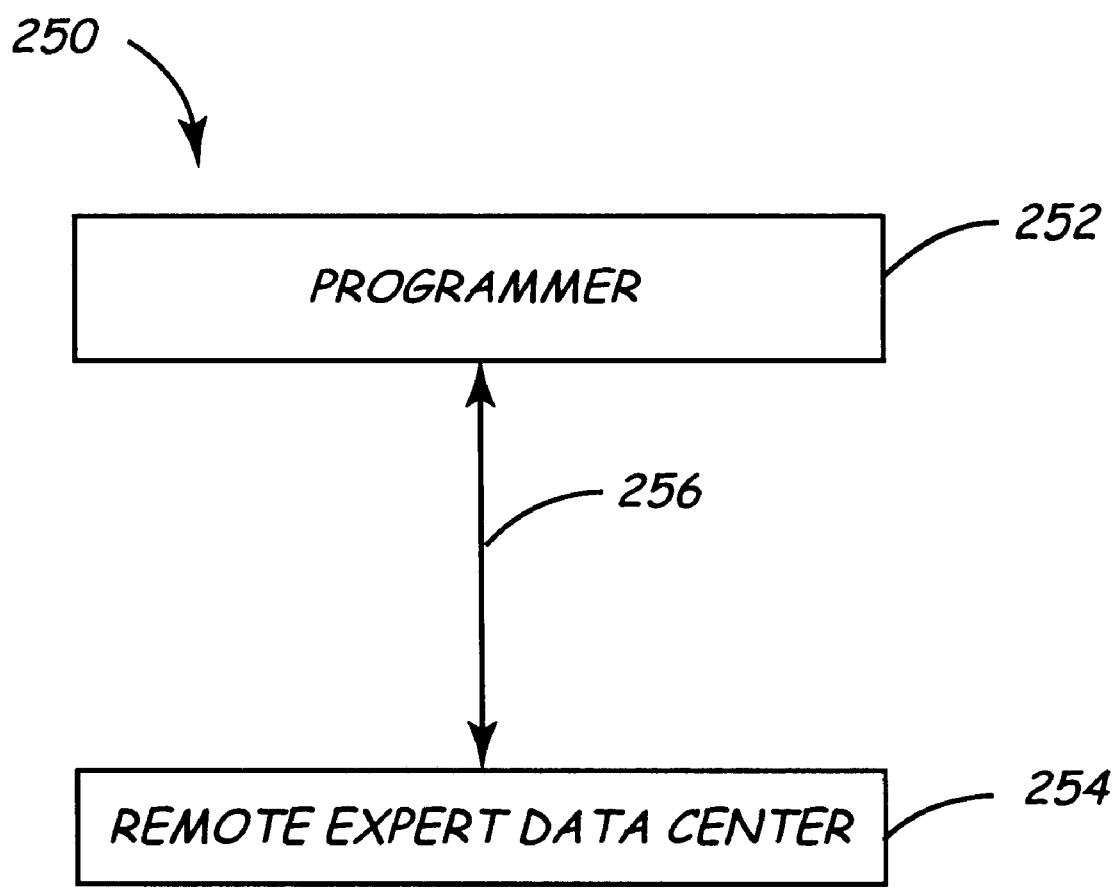
FIG. 6 is a simplified block diagram showing the overall system of the present invention.

FIG. 6 is a simplified block diagram illustrating the principle system used in conjunction with the invention. System 250 includes programmer 252 and remote expert data center 254 interconnected via data communications link/connection 256. Programmer 252 is located within medical facility 260 (shown in FIG. 6, such as a clinic, hospital, or physician's office.

Programming system 25 includes various instruments including programmer 200 and analyzer 210. The system is used to program one or more IMDs as shown in FIG. 4. IMD 10 is one of various devices such as a pacemaker, defibrillator or combinations thereof. IMDs may also represent a drug-delivery system, an electrical stimulator including a nerve or muscle stimulator, a neuro-stimulator, or a heart-assist device or pump. IMD 10, programmer 200, and analyzer 210 are microprocessor-based components capable of exchanging data and information between each other via a standard data communications link.

Remote expert data center 254 is a remote expert data centerized network system located at a distal location relative to programmer 252. For example, remote expert data center 254 can be located at a central location, such as at a corporate headquarters or manufacturing facility of the company which manufactures and owns programmer 252. As shown in FIG. 6, programmer 252 is connected to remote expert data center 254 via data communications link/connection 256. Data communications link/connection 256 can be one of a variety of links or interfaces, such as a local area network (LAN) connection, an internet connection, a telephone line connection, a satellite connection, a global positioning system (GPS) connection, a cellular connection, any combination thereof, or an equivalent communications link.

Data communications link/connection 256 permits the exchange of information between programmer 252 and remote expert data center 254. As discussed below, this novel feature of the invention provides one of the many distinguishing advances over the prior art.

FIG. 7 is a detailed block diagram illustrating the overall system used in conjunction with the invention. System 250 includes remote expert data center 254 and medical facility 260. Remote expert data center 254 is located at a distal location relative to medical facility 260. Remote expert data center 254 includes invoice preparation module 262 and inventory control module 264.

Medical facility 260, which is a hospital, a clinic, or a medical facility, can be located throughout the world and includes programmer 252 and accounting system 266. Patient 268 is also located at medical facility 260. Programmer 252 further includes programmer 200, analyzer 210, and RF head 258. Patient 268 further includes heart 8, IMD 10, and pacing and/or sensing leads 16 and 18.

Programmer 252 is connected to remote expert data center 254 via data communication links/connection 256. Similarly, remote expert data center 254 is connected to medical facility 260 via data communications link/connection 270. Data communication links/connections 256 and 270 can be one of a variety of links or interfaces, such as a LAN connection, an internet connection, a telephone connection, a satellite connection, a GPS connection, any combination thereof, or an equivalent communication link. Similarly, programmer 252 is in data communication with IMD 10 via RF head 258.

Once an implant procedure has been completed and medical components such as IMD 10 and pacing and/or sensing leads 16 and 18, are implanted into patient 268, it is critical that information identifying each medical component implanted into patient 268 is identified. Further, it is important that this identifying information is forwarded to the owner or manufacturer of the individual medical components so that the owner or manufacturer of the medical components can generate a bill for the implanted medical components and forward the bill to medical facility 260 for payment. Also, the owner or manufacturer of the medical components can control inventory of the implanted medical component at medical facility 260.

Prior art systems require a medical personnel, such as a physician, to prepare paperwork identifying the implanted medical components or physically enter the identifying information into a data entry system. The identifying information is then routed through medical facility 260, and eventually a report itemizing all implanted components is generated and transmitted to the owner or manufacture of the implantable medical devices. The owner or manufacturer of the implantable medical components must then generate an invoice and forward the invoice to medical facility 260 requesting payment. Additionally, the owner or manufacturer of the implanted medical components must track the inventory of various medical components at numerous medical facilities located throughout the world, including medical facility 260. This prior art process is manual labor intensive in that each step in the process requires a person to physically write down identifying information regarding each implanted medical component or enter identifying information for each implanted medical component into a data entry system. This entire process often takes weeks or even months to be completed. Therefore, at any given time, millions of dollars of medical components have been implanted into patients throughout the world; however, no billing or inventory information has been generated regarding these components.

With system 250 shown in FIG. 7, the above-discussed limitations in preparing an invoice and controlling inventory in a time-sensitive manner are alleviated. Specifically, with system 250, the inventory and invoicing processes are automated such that manual entries are no longer required.

As previously discussed, during the manufacture process of implantable medical components, such as IMD 10 and pacing and/or sensing leads 16 and 18, identifying information is programmed into a memory device of each component. For example, bar code information 234, serial number 236, and model number 238, shown in FIG. 7, are programmed into a microprocessor or ROM device during a manufacture process. During an implant procedure, programmer 252 is connected to patient 268 via RF head 258. Programmer 252, through specific use of programmer 200 and analyzer 210, both assesses the performance of pacing and/or sensing leads 16 and 18 during the implantation procedure and programs IMD 10. Therefore, programmer 252 is in data communication with IMD 10 and pacing and/or sensing leads 16 and 18 during an implant procedure. Programmer 252 is also in data communication with remote expert data center 254. Remote expert data center 254 is located at a distal location relative to programmer 252.

The identifying information of each implanted medical component is transmitted from programmer 252 to remote expert data center 254 via data communications link/connection 256. The identifying information for each implanted medical component is automatically forwarded to invoice preparation module 262 within remote expert data center 254. Invoice preparation module 262 automatically prepares an invoice or bill itemizing each implanted medical component. In one embodiment, each implanted medical component is identified by its identifying information, such as bar code information, serial number, and/or model number. The itemized invoice is then automatically forwarded to medical facility 260 via data communications link/connection 270. Similar to data communications link/connection 256, data communications link/connection 270 can be one of a variety of links or interfaces, such as a LAN connection, an internet connection, a telephone line connection, a satellite connection, a GPS connection, any combination thereof, or an equivalent thereof. In one embodiment of the present invention, the itemized bill or invoice is transmitted directly to accounting system 266 of medical facility 260 from remote expert data center 254 requesting payment.

The above-process is an entirely automated process which alleviates both operator error and time delays throughout the process due to operator inefficiency. With system 250, an invoice itemizing each remote medical component implanted into patient 268 can be automatically and instantaneously generated and transmitted to medical facility 260. The entire process takes seconds, rather than the weeks or months previously needed for this process.

Consistent with the above-discussed process, once the identifying information regarding each implanted medical component has been transmitted to remote expert data center 254, it is also instantaneously transmitted to inventory control module 264. Inventory control module 264 contains remote expert data center generated data regarding the quantity of specific medical components at various medical facilities throughout the world, including medical facility 260. It is important that medical facility 260 have the proper amount of each implantable medical component. The specific number of implantable medical components at medical facility 260 can vary depending upon the frequency of implantation of the specific medical component. However, it is critical that enough medical components are inventoried at medical facility 260 so that a specific medical component is available for an implant procedure. It is also important that medical facility 260 does not have an over abundant amount of specific medical components such that the medical component can no longer be implanted into a patient due to expiration of the component. For example, the Food and Drug Administration (FDA) has specific requirements regarding the age of a component before it can no longer be implanted into a patient. If the component has been manufactured prior to a specific date, the FDA may prevent implantation of the device.

Once the identifying information of each remote medical component has been transmitted to inventory control module 264, inventory control module 264 can automatically generate an inventory request to forward medical components to medical facility 260 to replace the implanted components.

FIG. 8 is a flow chart illustrating a method of automatically generating an invoice and forwarding the invoice to medical facility 260. Method 300 begins with step 302, wherein a memory portion 232 of implantable medical component 230 is programmed with identifying information providing identification of the implantable medical component. As previously discussed, a microprocessor or ROM device can be programmed with identifying information such as bar code information 234, serial number 236, and model number 238. At step 304, implantable medical component 230 is implanted into patient 268 as part of an implantable medical device system. In one embodiment of the present invention, implantable medical component 230 is either IMD 10 or pacing and/or sensing leads 16 and 18.

At step 306, an interface between the implantable medical device system and remote expert data center 254 located at a distal location relative to the implantable medical device system is initiated. As previously discussed, the interface, such as data communications link/connection 256 can be one of a variety of links or interfaces, such as a LAN connection, an internet connection, a telephone line connection, a satellite connection, a GPS connection, any combination thereof, or an equivalent communications link. At step 308, the identifying information of implantable medical component 230 implanted into patient 268 is transmitted to remote expert data center 254. In addition to transferring the identifying information, operator information regarding an implanting physician, timing information regarding a date and time of the implant procedure, and medical facility information regarding the location of the implant procedure is transmitted to remote expert data center 254, as shown at step 310.

At step 312, an automated invoice is prepared on remote expert data center 254 for implantable medical component 230 based upon the identifying information. The preparation of the invoice occurs within invoice preparation module 262. The invoice may also include information regarding the implanting physician, the date and time of the implant procedure, and the location of the implant procedure. The invoice is transmitted to medical facility 260 where the implant procedure occurred, as shown at step 314. In one embodiment of the present invention, the invoice is transmitted directly to accounting system 266 of medical facility 260 via data communications link/connection 270.

FIG. 9 is another flow chart illustrating a method of controlling inventory of medical components within medical facility 260. Method 320 includes steps 302–310 which are identical to steps 302–310 of FIG. 10, and have been labeled as such. Method 320 deviates from method 300 shown in FIG. 10 at step 322 where the identifying information of implantable medical component 230 is transmitted to inventory control system 264. At step 324, the inventory of medical component 230 at medical facility 260 is controlled. In one preferred embodiment, inventory control module 264 automatically generates a transmittal order requiring the owner or manufacturer of remote medical component to transmit a replacement of implantable medical component 230 to medical facility 260 to replace the implanted component. Therefore, the inventory of a specific medical component at medical facility 260 is precisely controlled such that a proper number of medical components are within the inventory of medical facility 260.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A system for automatic inventory control and invoice preparation for implantable medical devices at a medical facility, comprising:

an implantable medical device having identifying information stored therein;

a programmer at the medical facility in bi-directional data communication with the implantable medical device during an implant procedure for the implantable medical device to access the stored identifying information; and a remote expert data center in data communication with the programmer over a first network link to obtain the implantable medical device identifying information accessed by the programmer;

said remote expert data center having data processing software, including an invoice preparation module and an inventory control module, to analyze the implantable medical device identifying information obtained from the programmer and generate an itemized invoice of the implantable medical device;

said remote expert data center being in data communication with the medical facility over a second network link to transmit an itemized invoice data for the implantable medical device implanted during the implant procedure; and said remote expert data center being in data communication with a manufacturer of the implantable medical device over a third network link to transmit an order for an inventory replacement of the implantable medical device.

2. The system of claim 1 wherein the programmer records information during the implant procedure regarding the implanting physician, the date and time of the implant procedure, and location of the medical facility for transmission to the expert data center along with the implantable medical device identifying information.

3. The system of claim 1 wherein the implantable medical device is selected from a group consisting of a pacemaker, a defibrillator, a drug delivery system, a neuro-stimulator, a muscle stimulator, or a heart-assist pump.

4. The system of claim 1 wherein the stored implantable medical device identifying information is selected from a group consisting of bar code information, serial number information, or model number information.

5. The system of claim 1 wherein each of the first, second and third network links for data communication is selected from a group consisting of an Internet connection, a telephone line connection, a satellite connection, or a local area network connection.

* * * * *